(12) United States Patent
Takagi et al.

(10) Patent No.: US 7,399,629 B2
(45) Date of Patent: Jul. 15, 2008

(54) CELL/TISSUE CULTURE APPARATUS

(75) Inventors: Takao Takagi, Shimizu-ken (JP); Setsuo Watanabe, Shizuoka-ken (JP)

(73) Assignee: Takagi Industrial Co., Ltd., Shizuoka-Ken (JP)

( * ) Notice: Subject to any disclaimer, the term of this patent is extended or adjusted under 35 U.S.C. 154(b) by 732 days.

(21) Appl. No.: 10/475,183

(22) PCT Filed: Feb. 22, 2002

(86) PCT No.: PCT/JP02/01592

§ 371 (c)(1),
(2), (4) Date: Mar. 24, 2004

(87) PCT Pub. No.: WO02/086056

PCT Pub. Date: Oct. 31, 2002

(65) Prior Publication Data

US 2004/0235150 A1    Nov. 25, 2004

(30) Foreign Application Priority Data

Apr. 17, 2001   (JP) ............................. 2001-118757

(51) Int. Cl.
*C12M 3/00* (2006.01)
(52) U.S. Cl. ............... 435/289.1; 435/293.1; 435/302.1
(58) Field of Classification Search ............. 435/289.1, 435/293.1, 286.5, 302.1; 73/54.28; 623/915

See application file for complete search history.

(56) References Cited

U.S. PATENT DOCUMENTS 5,928,945 A * 7/1999 Seliktar et al. .............. 435/395

(Continued)

FOREIGN PATENT DOCUMENTS

DE   3714708 A1 * 2/1988

(Continued)

OTHER PUBLICATIONS

Blackman et al. 'In Vitro Cell Shearing Device to Investigate the Dynamic Response of Cells in a Controlled Hydrodynamic Environment.' Annals of Biomedical Engineering. vol. 28 (2000), pp. 363-372.*

(Continued)

*Primary Examiner*—William H Beisner
(74) *Attorney, Agent, or Firm*—Connolly Bove Lodge & Hutz LLP

(57) ABSTRACT

The invention provides a cell/tissue culture apparatus capable of applying an optional physical stimulation to a material to be cultivated serving as a cell or tissue to be cultivated and of protecting the material to be cultivated from contamination of various bacteria and so forth. The cell/tissue culture apparatus comprises a chamber (culture chamber 8) for accommodating the material to be cultivated (matrix 10) therein and receiving a culture fluid (18), a disc (24) rotatably installed in the chamber for applying a physical stimulation to the material to be cultivated by way of the culture fluid (18) when it is rotated, and rotary driving means (external rotation body 32 and motor 40) for applying a rotating force to the disc from an outside of the chamber in a state where it does not contact the disc, and it can apply an optional physical stimulation to the material to be cultivated serving as the cell or tissue to be cultivated, protecting the material to be cultivated from contamination of bacteria and so forth.

10 Claims, 17 Drawing Sheets

U.S. PATENT DOCUMENTS 6,121,042 A    9/2000  Peterson et al.

FOREIGN PATENT DOCUMENTS

| JP | 03007575 | 1/1991 |
| JP | 11239474 | 9/1999 |
| WO | WO-98/225573 | 5/1998 |
| WO | WO-9822573 | 5/1998 |

OTHER PUBLICATIONS

International Search Report (Apr. 2002).
Supplementary European search report issued in corresponding European Application No. 02700699.8 Mar. 27, 2007.

* cited by examiner

CELL/TISSUE CULTURE APPARATUS

TECHNICAL FIELD

The invention relates to an apparatus for cultivating a cell or tissue (hereinafter referred to as cell/tissue culture apparatus) for use in the culture of a cell or tissue, and so forth to which a tissue engineering is applied, more particularly relates to a cell/tissue culture apparatus for efficiently realizing a metabolism function of a cell or tissue when performing an in vitro culture of the cell or tissue of a living body such as human body and so forth, and applying a physical stimulation necessary for prolongation, differentiation, and acceleration of a cell to a material to be cultivated.

BACKGROUND ART

There has been conventionally employed a method of performing an in vitro culture of a cell or tissue of a living body such as human body, wherein a temperature, a humidity, a carbon dioxide concentration, an oxygen concentration in an incubator (culture housing) are maintained at proper conditions, and the cell is cultivated in the incubator. The cell or tissue is placed in a culture fluid in a suspending state, and it is fixed to an interior or surface of a gel in which the culture fluid ingredient is contained, thereby proliferating and growing the cell or tissue, or the cell or tissue is transplanted in a material, that is exemplified as a matrix or scaffold, a carrier or a mold and so forth (hereinafter referred to as "matrix"), thereby proliferating and growing the cell or tissue in the matrix.

Meanwhile, it is important to apply a physical stimulation to a cell or tissue to be cultivated in addition to an environment condition such as a temperature, a humidity, a carbon dioxide concentration, an oxygen concentration for proliferating and growing the cell or tissue. Such a physical stimulation is an indispensable constituent for facilitating differentiation and growth of the cell or tissue and for growing the cell or tissue to be rendered closer to that in the living body. For a technology for applying a physical stimulation to the cell or tissue for proliferating and growing the cell or tissue, there are, for example, JP 2001-504697A entitled "Application of shear flow stress to chondrocytes", U.S. Pat. No. 6,121,042 entitled "Apparatus and method for simulating in vivo conditions while seeding and culturing three-dimensional tissue constructs", and so forth.

Although it is necessary to add a dynamic condition such as a physical stimulation to a static condition, a so-called culture environment such as a temperature, a humidity, a carbon dioxide concentration, an oxygen concentration for proliferating and growing the cell or tissue, there is a possibility that the control of the dynamic condition together with the static condition renders a control mode complex, and a factor caused by the invasion of various bacteria, and so forth increases. It is an important challenge to protect a material to be cultivated from contamination of various bacteria.

Accordingly, it is a first object of the invention to provide a cell/tissue culture apparatus capable of applying a physical stimulation, which is necessary for proliferation and growth of the cell or tissue, to a material to be cultivated serving as a cell or tissue to be cultivated.

It is a second object of the invention to provide a cell/tissue culture apparatus for protecting the material to be cultivated from contamination of various bacteria and so forth.

DISCLOSURE OF THE INVENTION

The cell/tissue culture apparatus of the invention is characterized in comprising a chamber 8 for accommodating a material to be cultivated (matrix 10) therein and receiving a culture fluid 18, a disc 24 rotatably installed in the chamber 8 for applying a physical stimulation to the material to be cultivated by way of the culture fluid 18 when it is rotated, and rotary driving means (an external rotary body 32 and a motor 40) for applying a rotating force to the disc 24 from an outside of the chamber 8 in a state where it does not contact the disc 24.

With such a cell/tissue culture apparatus, a rotating force is applied from the rotary driving means to the disc in the chamber to rotate the disc, thereby applying a physical stimulation to the material to be cultivated. In this case, the rotation of the disc produces rotating flow in the culture fluid inside the chamber, and the rotating flow of the culture fluid becomes a physical stimulation to be applied to the material to be cultivated. Since the physical stimulation is equivalent to that on a living body at specific part of the human body, it contributes to the growth and so forth of the cell or tissue at that part.

According to the cell/tissue culture apparatus of the invention, it is characterized in that the physical stimulation is a shear stress. That is, the culture fluid flows as the disc is rotated owing to a viscosity of the culture fluid, and hence a shear stress is applied to a part where the culture fluid contacts the material to be cultivated owing to the flow of the culture fluid and viscosity of the culture fluid, which becomes the physical stimulation necessary for the proliferation and growth of the cell or tissue.

According to the cell/tissue culture apparatus of the invention, it is characterized in that the rotary driving means applies the rotating force to the disc, while magnetic coupling means (magnetic bodies 30 and magnets 36) is interposed between the disc and the rotary driving means. That is, it is possible to apply the rotating force to the disc in a non-contact state where the rotary driving means does not contact the disc, resulting in the contribution to the prevention of contamination in the chamber.

According to the cell/tissue culture apparatus of the invention, it is characterized in that the rotary driving means is a motor 40. That is, the motor 40 can obtain a revolution as desired so as to control the rotating force with an optional rotary pattern, resulting in the contribution to the realization of a physical stimulation as desired.

According to the cell/tissue culture apparatus of the invention, it is characterized in further comprising control means (controller 60) for controlling the rotating force of the rotary driving means with an optional pattern. That is, a mode of rotating force is controlled with an optional pattern, thereby allowing the physical stimulation to be varied variously.

According to the cell/tissue culture apparatus of the invention, it is characterized in that a culture unit 4 in which the chamber is formed is rendered in a hermetically sealed state, and it is detachably attached to a culture circuit 16 for circulating the culture fluid therein. That is, the material to be cultivated can be moved for every unit of the culture unit, and the culture unit 4 can be easily hermetically sealed so that the material to be cultivated can be protected from the contamination of various bacteria.

According to the cell/tissue culture apparatus of the invention, it is characterized in that the disc is set such that a rotary shaft thereof can be moved in a direction orthogonal to its axis. That is, since the rotary shaft can be moved in a direction orthogonal to its axis, the rotation of the disc can be varied to obtain a complex rotary pattern, thereby enhancing the degree of freedom of the physical stimulation to be applied to the material to be cultivated According to the cell/tissue culture apparatus of the invention, it is characterized in further comprising photographing means (CCD camera 130) for photographing the material to be cultivated in the chamber. That is, the photographing of the material to be cultivated in the chamber to obtain image data forms important data for the proliferation and the growth of the material to be cultivated.

According to the cell/tissue culture apparatus of the invention, it is characterized in further comprising a culture unit which is transparent as a part or as a whole and photographing means, wherein the material to be cultivated is accommodated and cultivated in the chamber formed in the culture unit, and the material to be cultivated can be photographed by the photographing means from an outside of the chamber. That is, the material to be cultivated can be photographed from the outside of the chamber without disturbing a culture environment in the chamber, thereby obtaining its image data.

Other objects, features, advantages and so forth of the invention are more clarified from the description of the mode for carrying out the invention and the embodiments as illustrated in the drawings.

BEST MODE FOR CARRYING OUT THE INVENTION

The invention and the mode for carrying out the invention are now described in detail with reference to the embodiments as illustrated in the attached drawings.

Figure 1:
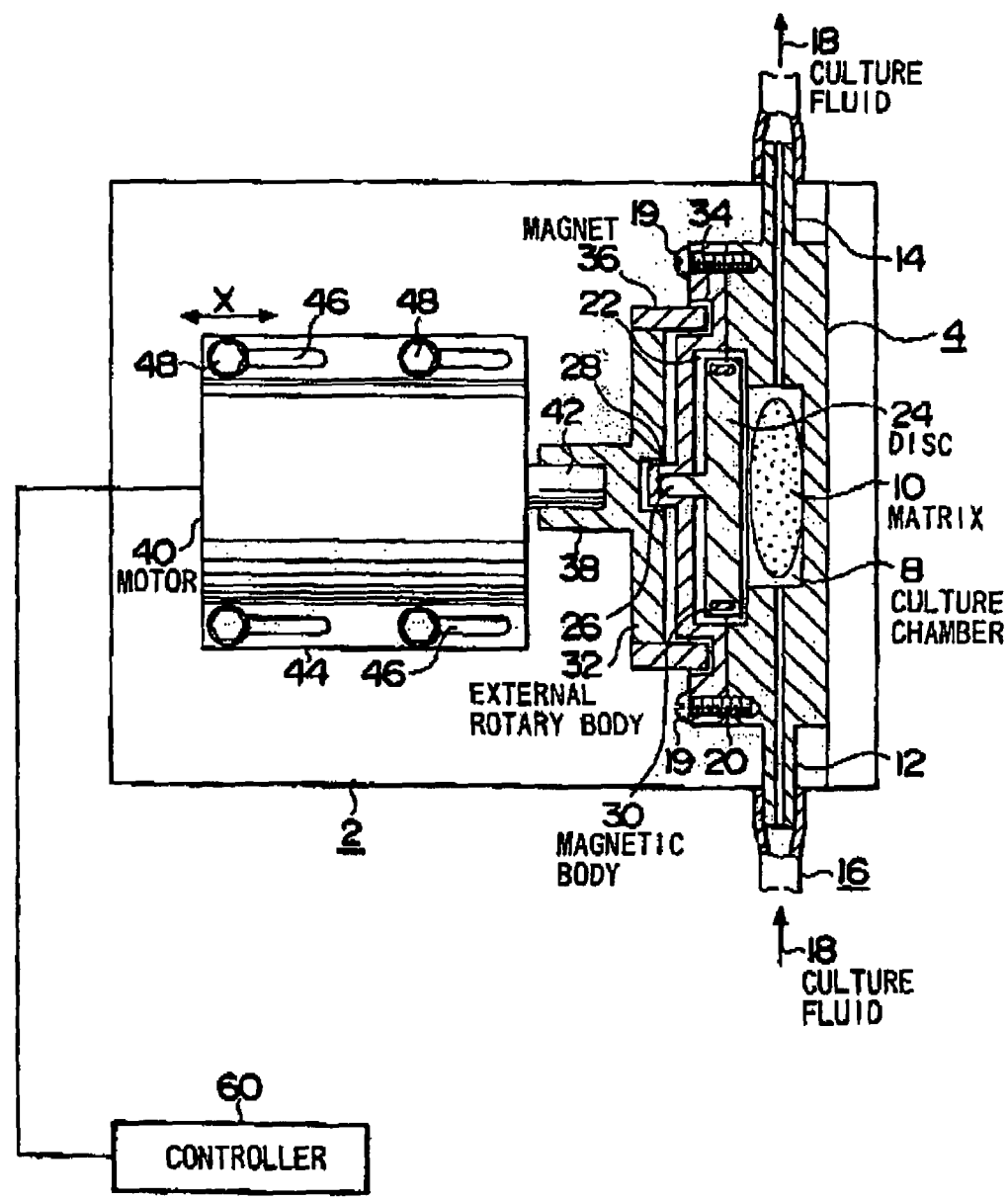
FIG. 1 is a partially sectional view showing a cell/tissue culture apparatus according to a first embodiment of the invention.
Figure 2:
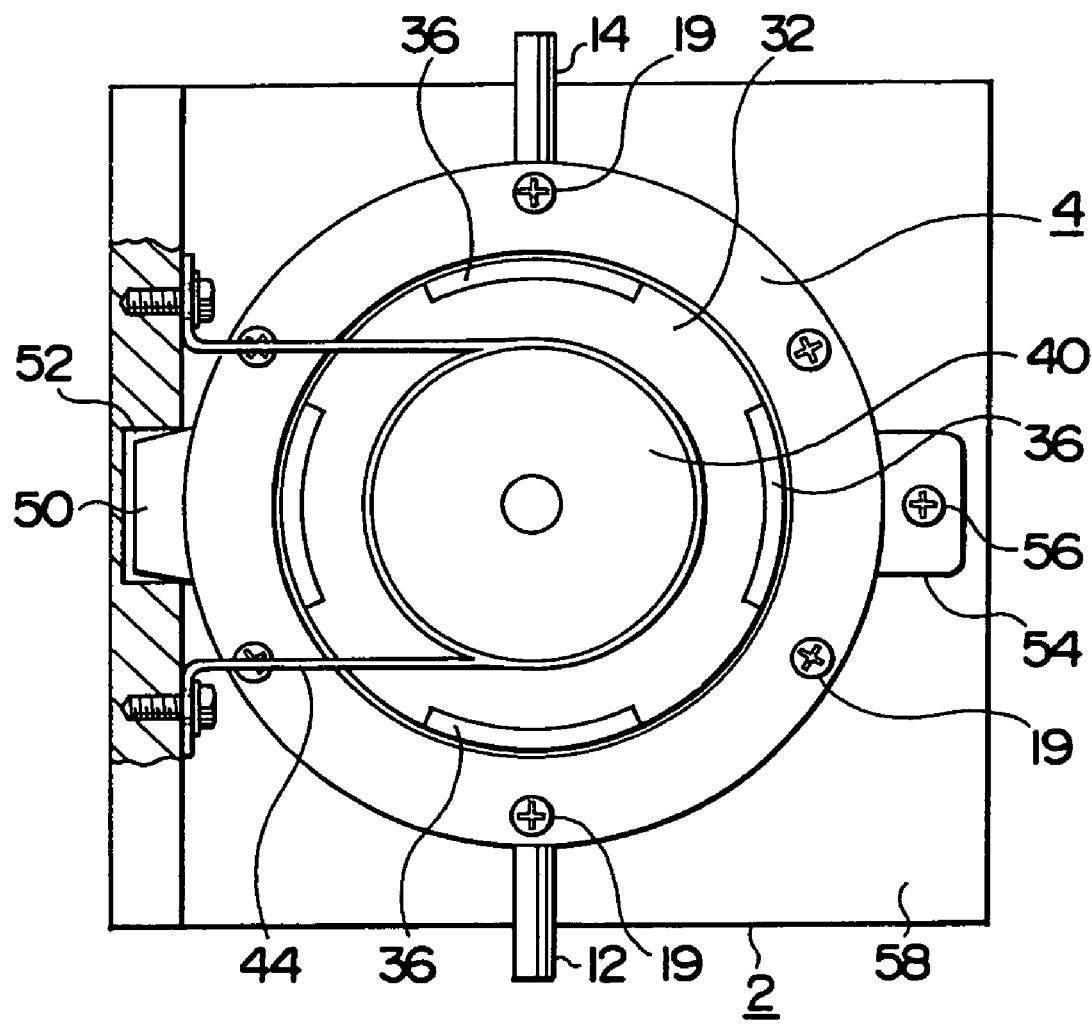
FIG. 2 is a plan view showing a culture unit.
Figure 3:
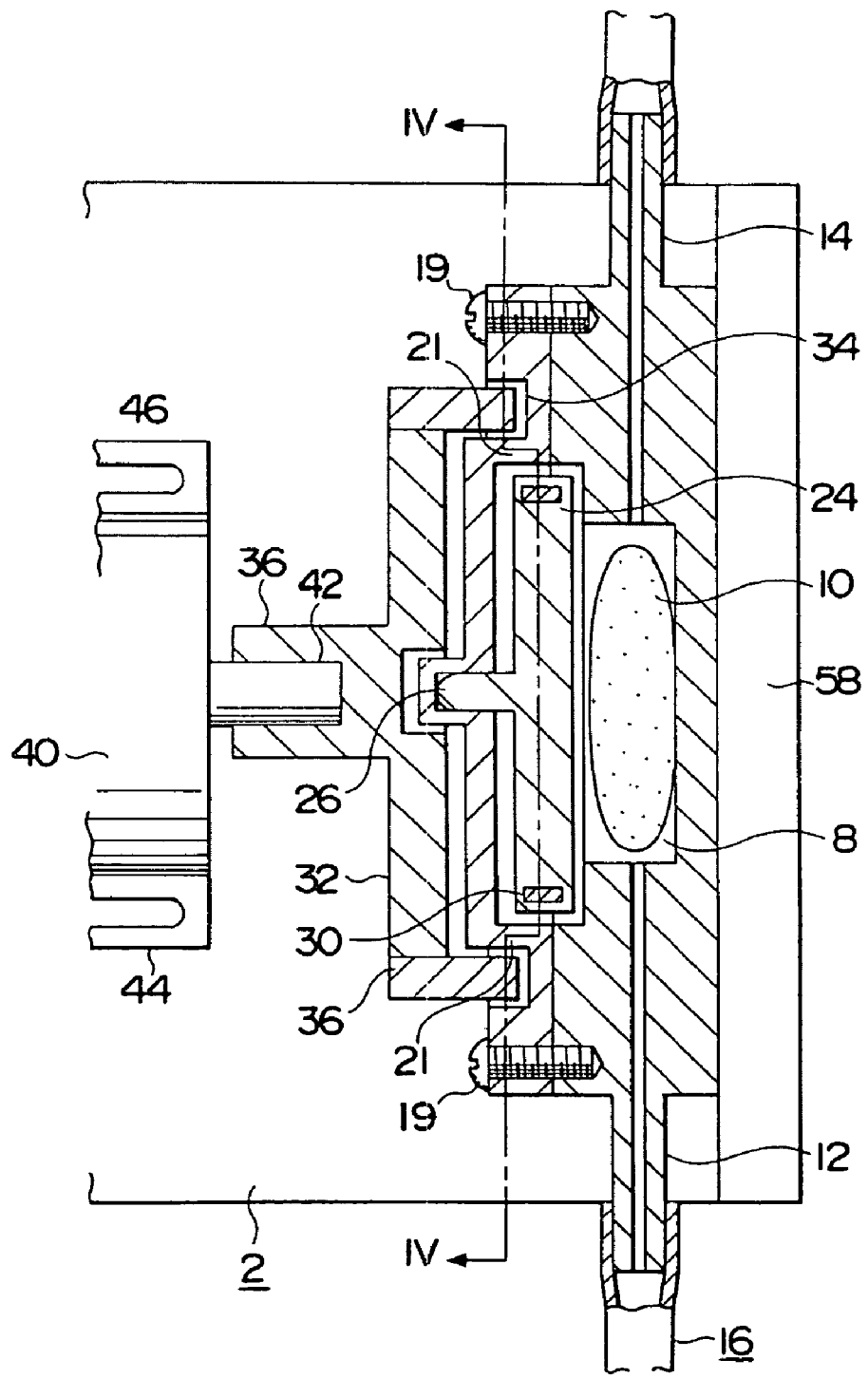
FIG. 3 is an enlarged sectional view showing a main part of the culture unit.
Figure 4:
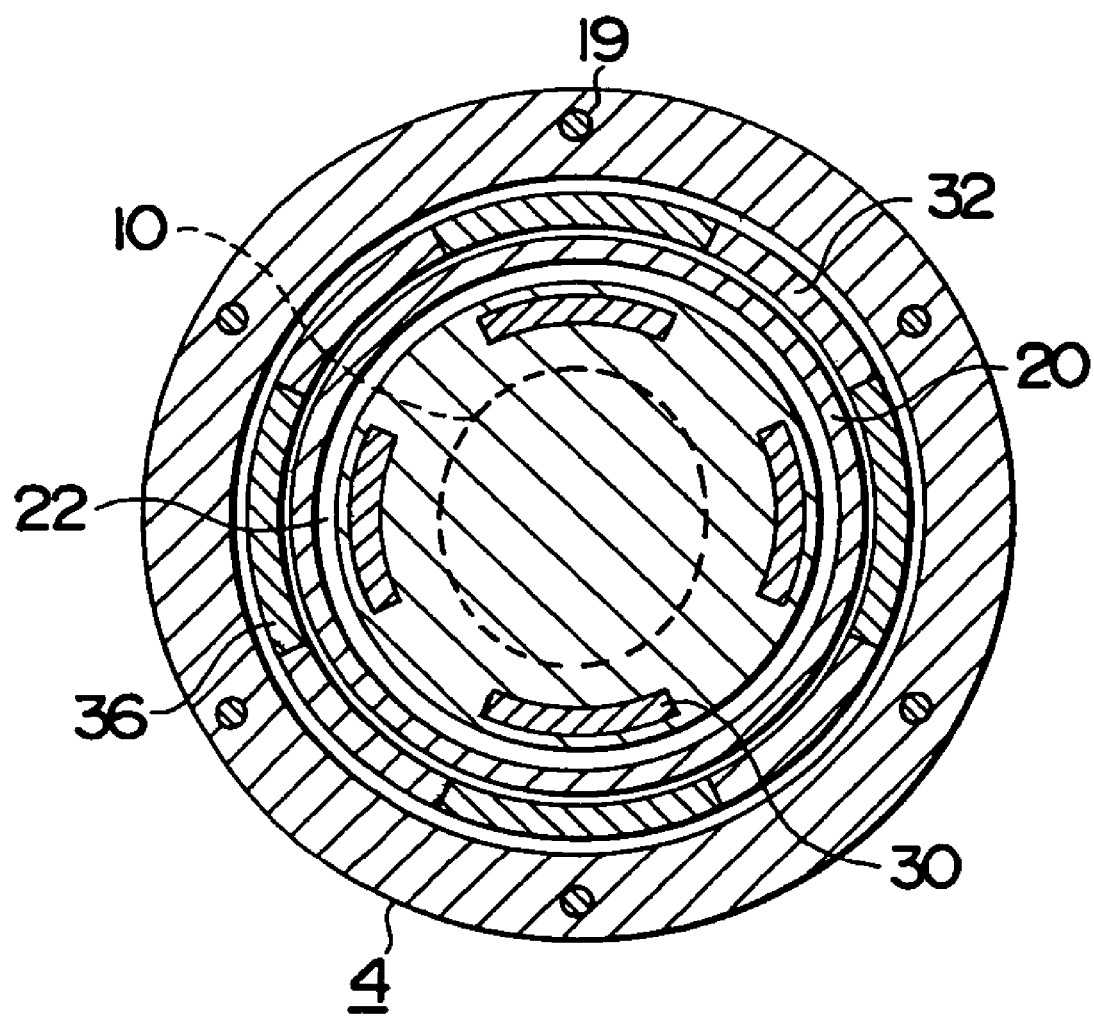
FIG. 4 is a sectional view of the culture unit taken along the ling IV-IV shown in FIG. 3.
Figure 5:
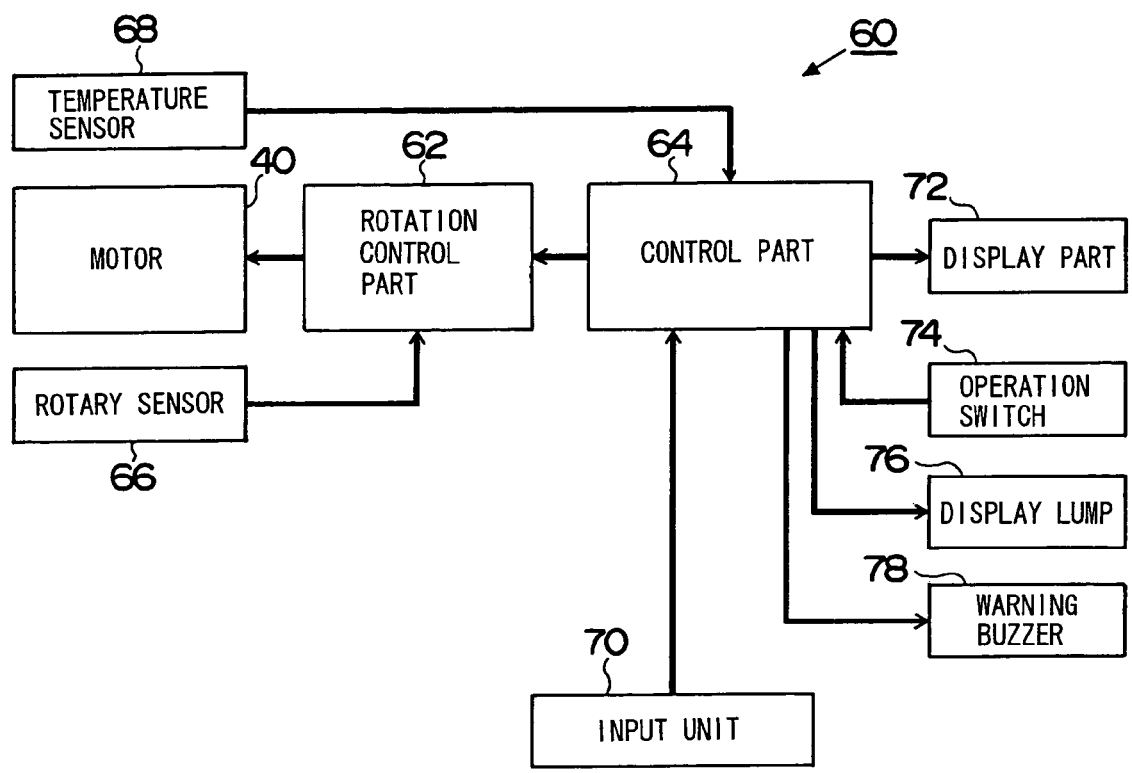
FIG. 5 is a block diagram showing a controller.

FIGS. 1 to 5 show a cell/tissue culture apparatus according to the first embodiment of the invention, wherein FIG. 1 shows a culture unit and so forth on a culture circuit, FIG. 2 is a plan view of the culture unit, FIG. 3 is an enlarged sectional view showing a main part of the culture unit, FIG. 4 is a sectional view of the culture unit taken along the line IV-IV shown in FIG. 3, and FIG. 5 shows a controller.

A culture unit 4 serving as a culture part is detachably installed on an apparatus body 2, and the culture unit 4 has a high grade heat resistant property and is made up of stainless steel as well as a resin material from which a material adversely affecting on a living body does not liquate out, for example, fluorine resin, PEEK, high grade heat resistant polypropylene, silicone and so forth. A culture chamber 8 serving as a hermetically sealed culture space is formed in the culture unit 4, and a matrix 10 serving as a material to be cultivated is accommodated in the culture chamber 8.

Ports 12, 14 are formed in the culture unit 4 so as to penetrate the culture chamber 8 in a diameter direction, and the culture unit 4 is connected to a culture circuit 16 by way of the ports 12, 14. The culture circuit 16 is means for circulating a culture fluid 18 serving as medium for supplying nutrition to the matrix 10, and the culture fluid 18 is introduced into the culture chamber 8 through the port 12, and flows from the culture chamber 8 to the port 14. That is, the culture fluid 18 is supplied to the culture chamber 8 and fluid flow is generated in the culture chamber 8.

A chamber cover 20 is attached to the back side of the culture unit 4 by a plurality of fixing bolts 19. For fixing means of the chamber cover 20, any means other than the fixing bolts 19, for example, a clapper and so forth may be used. A disc accommodation space 22 is formed at the side of the chamber cover 20, and a circular disc 24 is rotatably installed in the disc accommodation space 22 according to the first embodiment. The disc 24 has a flat face at the side of the matrix 10 and has a supporting shaft 26 at the center of the back side thereof, wherein when the supporting shaft 26 is inserted into a bearing part 28 of the chamber cover 20, the disc 24 can be rotatably supported in the disc accommodation space 22.

A plurality of circular arc magnetic bodies 30 made up of a steel plate and so forth are inserted into the disc 24 with predetermined angular intervals at the outer periphery thereof. An external rotary body 32 is installed at the outer periphery of the disc 24 while interposing the chamber cover 20 therebetween, and a part of the chamber cover 20 is interposed between the external rotary body 32 and the disc 24. That is, a part of the chamber cover 20 is swelled and a part of the external rotary body 32 is inserted into an annular recess part 34 which is formed in the outer surface of the chamber cover 20 in a non-contact state therebetween. Magnets 36 having the same number as the magnetic bodies 30 of the disc 24 are attached to the outer periphery of the external rotary body 32. That is, the external rotary body 32 and the disc 24 are rendered in a magnetic non-contact connection by the magnets 36 and the magnetic bodies 30 serving as magnetic connecting means. The positional relationship among a wall 21 of the chamber cover 20, the disc accommodation space 22, the disc 24, the external rotary body 32, the matrix 10, and so forth in the culture unit 4 is illustrated in FIG. 3.

A rotary shaft 42 of a motor 40 serving as rotary driving means is attached to a fixed part 38 provided at the center of the external rotary body 32, and the rotating force of the motor 40 is applied to the disc 24. A plurality of long holes 46 are defined in a fixed tool 44 of the motor 40, and the motor 40 is positioned and fixed to the apparatus body 2 by the long holes 46 and the plurality of fixing bolts 48. Denoted by an arrow X shows the movement of the motor 40 and its direction when the motor 40 is detachably attached to the apparatus body 2.

A retaining projection 50 is formed on the periphery of the culture unit 4, and it is inserted in a retaining recess 52 of the apparatus body 2, thereby stopping the culture unit 4 from turning around on the apparatus body 2 and positioning the culture unit 4 on the apparatus body 2 while a fixed piece 54 formed on the periphery of the culture unit 4 is fixed to an upright wall part 58 of the apparatus body 2 by a fixing bolt 56.

A controller 60 serving as rotation control means is provided in the motor 40. The controller 60 has, for example, as shown in FIG. 5, a rotation control part 62 for controlling the rotation of the motor 40 such as the flowing of a driving current to the motor 40, and so forth, and a control part 64 for executing programmed control for setting a rotary pattern and so forth. The motor 40 has a rotary sensor 66 for detecting the rotation thereof, and a temperature sensor 68 for detecting a temperature thereof, wherein a rotation detection signal is supplied to the rotation control part 62 and a temperature detection signal is supplied to the control part 64 as a control input, respectively. The control part 64 has a CPU serving as processing means, a ROM, a RAM, and so forth serving as storage means, and a program such as rotation conditions and so for this set from an externally connected input unit 70. The control part 64 has a display part 72, an operation switch 74 for giving an operation instruction, a display lump 76 exemplified as operation display means, and a warning buzzer 78 serving as warning means.

Figure 6:
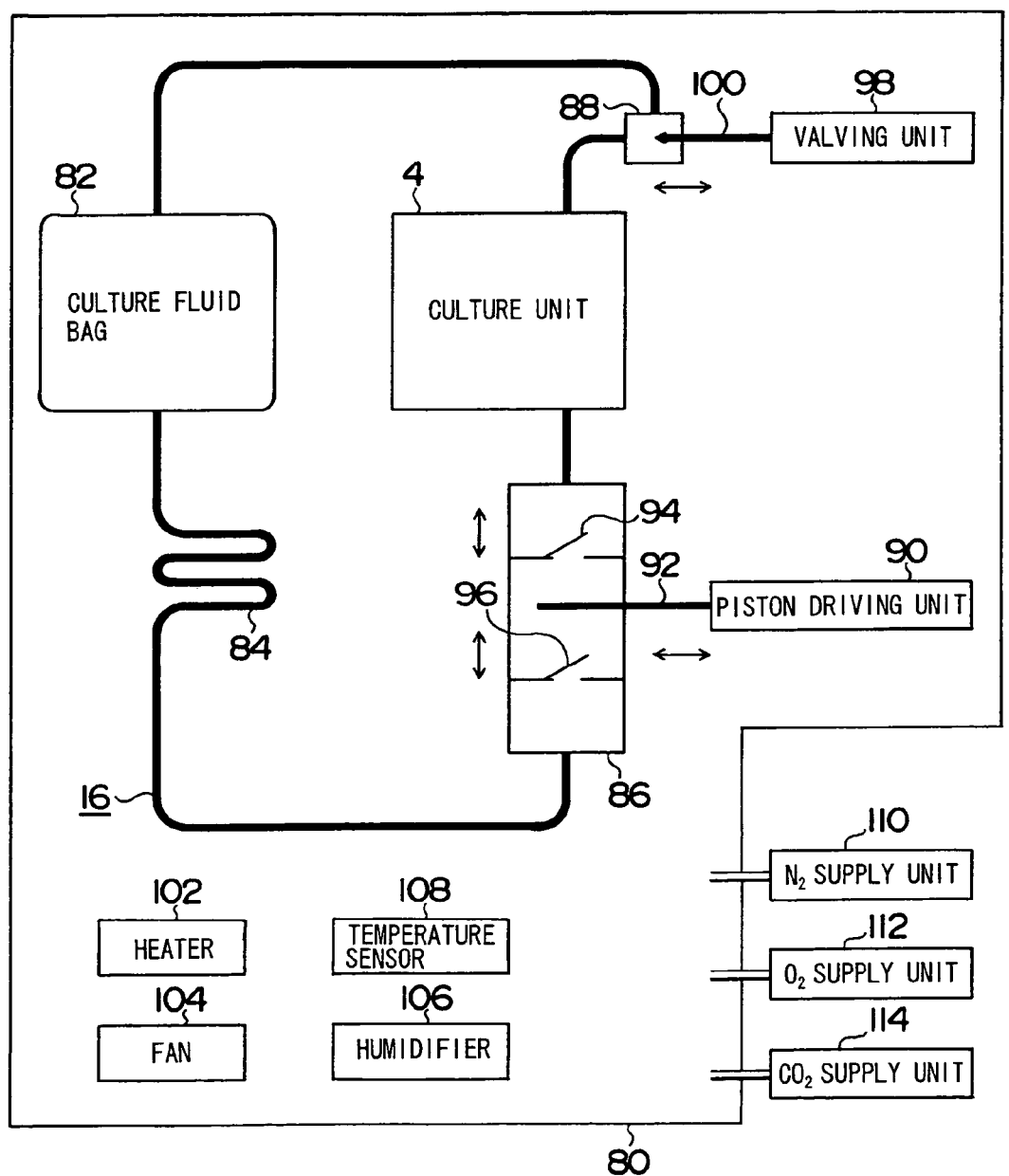
FIG. 6 is a view showing a cell or tissue culture system.

According to the cell/tissue culture apparatus, there is formed the culture circuit 16, for example, as shown in FIG. 6, wherein the culture circuit 16 is accommodated in a culture housing 80 forming an optimum culture environment. There are provided in the culture circuit 16 a culture fluid bag 82 for storing the culture fluid 18 therein, a gas absorption tube 84 for allowing the culture circuit 16 to absorb gas, a fluid supply valve 86 for performing circulation of the culture fluid 18, and a pressure regulating valve 88. A piston 92 which is advanced or retracted by a piston driving unit 90 is provided in the fluid supply valve 86, wherein when the piston 92 is advanced, a valve 94 is opened and a valve 96 is shut while when the piston 92 is retracted, the valve 94 is shut and the valve 96 is opened, thereby effecting delivery of a predetermined amount of culture fluid 18 like the heart. A valve 100, which is advanced and retracted by a valving unit 98, is provided in the pressure regulating valve 88, wherein when the valve 100 is advanced, the pressure regulating valve 88 is shut while when the valve 100 is retracted, the pressure regulating valve 88 is opened, thereby performing pressure regulation of the culture fluid 18 in the culture circuit 16.

The culture housing 80 is provided with a heater 102 serving as heating means, a fan 104 serving as blowing means, a humidifier 106 serving as means for setting a humidity as desired, and a temperature sensor 108, and to which $N_2$ is supplied from an $N_2$ supply unit 110, $O_2$ is supplied from an $O_2$ supply unit 112, and $CO_2$ is supplied from a $CO_2$ supply unit 114, thereby forming an optimum culture environment adapted for the proliferation and growth of the cell or tissue.

Figure 7:
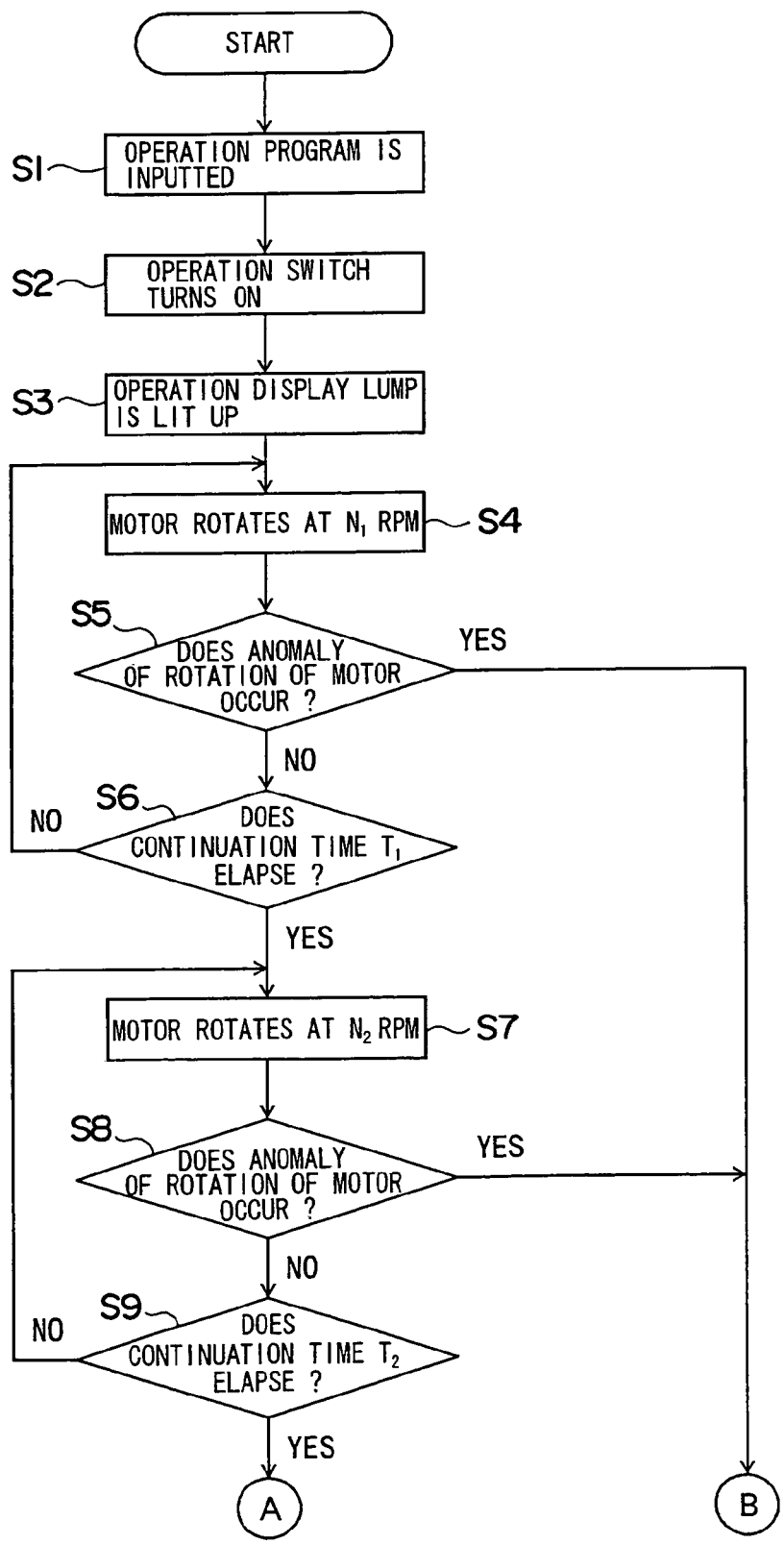
FIG. 7 is a flowchart showing a former half part of a control program.
Figure 8:
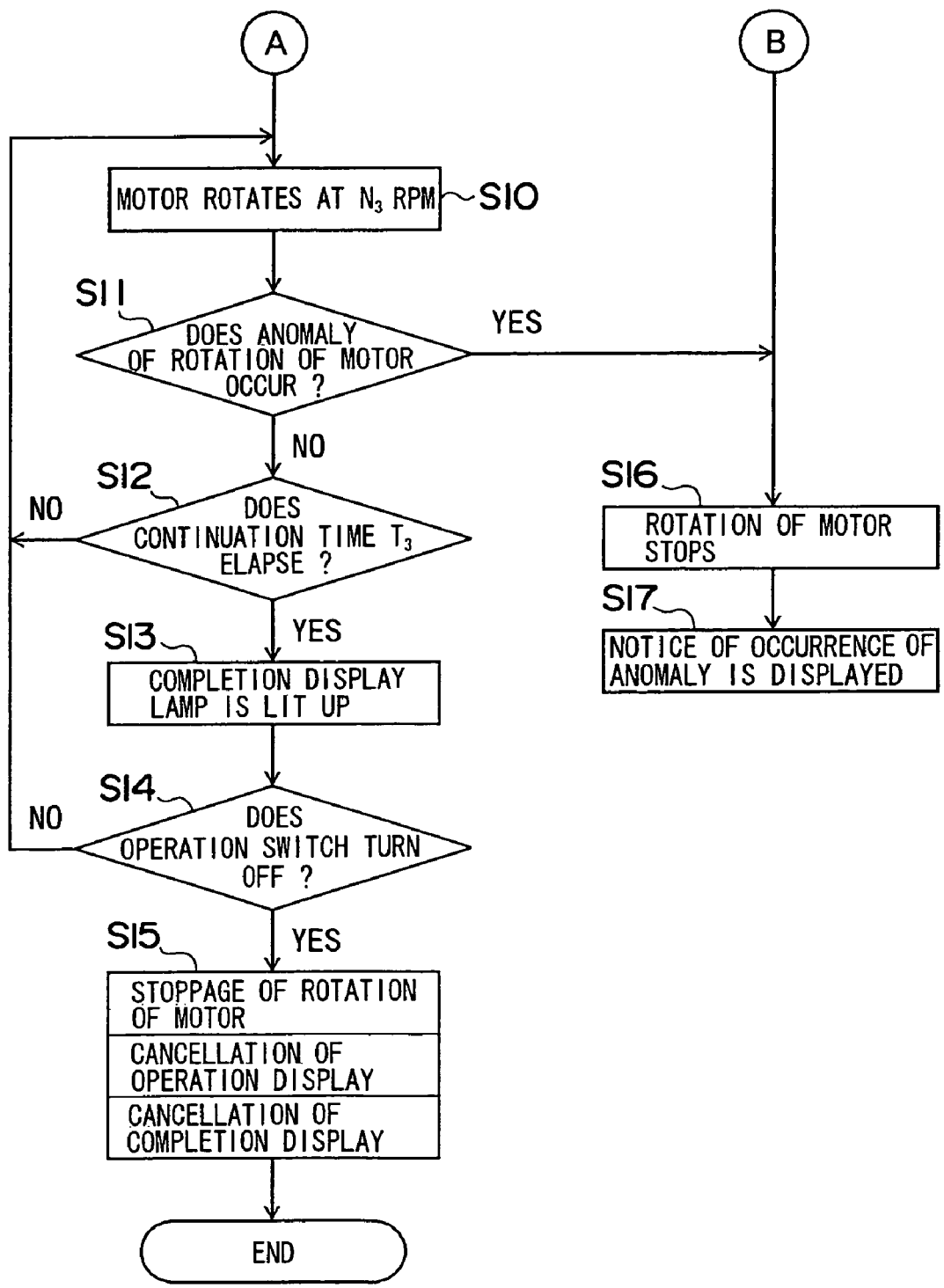
FIG. 8 is a flowchart showing a latter half part of the control program shown in FIG. 7.

A culture processing using the cell/tissue culture apparatus is next described with reference to flowcharts shown in FIG. 7 and FIG. 8. In FIG. 7 and FIG. 8, depicted by circled A and B show connecting symbols of the divided flowcharts extending over FIGS. 7 and 8.

In step S1, the controller 60 is set at an operation state, and an operation program is inputted through the input unit 70, thereby setting conditions such as revolutions of $N_1$ rpm, $N_2$ rpm, $N_3$ rpm of the disc 24 and rotation continuation time (hereinafter referred to as continuation time) $T_1$, $T_2$, $T_3$ and so forth corresponding to each culture stage. After setting such conditions, when the operation switch 74 turns ON in step S2, the program goes to step S3 where an operation indication is displayed on the display part 72 and the display lump 76 is lit up.

In step S4, the motor 40 rotates at $N_1$ rpm, and the rotating force of the motor 40 is transmitted from the external rotary body 32 to the disc 24 through the magnetic connection, thereby producing rotating flow of the culture fluid 18 in the culture chamber 8. The rotating flow is produced along the surface of the disc 24, for example, as shown by a plurality of arrows Y having different length shown in FIG. 9, and it is fluid flow which is differentiated in linear velocity at a central side and peripheral side. The length of each arrow Y indicates the velocity of fluid flow.

During the rotation of the motor, in step S5, it is decided whether anomaly of the rotation of the motor occurs or not based on detection outputs of the rotary sensor 66 and the temperature sensor 68, and when there dose not occur anomaly, the program goes to step S6. In step S6, it is decided whether the continuation time $T_1$ elapses or not, and the detection and decision of the rotation of the motor 40 at $N_1$ rpm and anomaly of the rotation of the motor 40 are effected until the continuation time $T_1$ elapses.

When the continuation time $T_1$ elapses, the program goes to step S7 where the rotation of the motor 40 shifts from $N_1$ rpm to $N_2$ rpm, then the program goes to step S8 where during the rotation of the motor 40, it is decided also whether anomaly of the rotation of the motor occurs or not based on the detection outputs of the rotary sensor 66 and the temperature sensor 68, and when there dose not occur anomaly, the program goes to step S9. In step S9, it is decided whether the continuation time $T_2$ elapses or not, and the detection and decision of the rotation of the motor 40 at $N_2$ rpm and anomaly of the rotation of the motor 40 are effected until the continuation time $T_2$ elapses.

When the continuation time $T_2$ elapses, the program goes to step S10 where the rotation of the motor 40 shifts from $N_2$ rpm to $N_3$ rpm, then the program goes to step S11 where during the rotation of the motor 40, it is also decided whether anomaly of the rotation of the motor occurs or not based on the detection outputs of the rotary sensor 66 and the temperature sensor 68, and when there dose not occur anomaly, the program goes to step S12. In step S12, it is decided whether the continuation time $T_3$ elapses or not, and the detection and decision of the rotation of the motor 40 at $N_3$ rpm and anomaly of the rotation of the motor 40 are effected until the continuation time $T_3$ elapses.

When the continuation time $T_3$ elapses, the program goes to step S13 where a completion display is effected, then the program goes to step S14 where it is decided whether the operation switch 74 turns OFF or not, and the rotation of the motor 40 continues at $N_3$ rpm until the operation switch 74 turns OFF. This is effected for preventing the death of cell or tissue on the matrix 10.

When the operation switch 74 turns OFF, the program goes to step S15 where stoppage of the rotation of the motor, and the cancellation of the operation display and completion display are effected, thereby completing the culture program.

In the case where the anomaly of the rotation of the motor is turned out in step S5, step S8, and step S11, the program goes to step S16 where the rotation of the motor stops, then the program goes to step S17 where a notice of the occurrence of anomaly is displayed on the display part 72 as a warning display, and the warning buzzer 78 is sounded.

Meanwhile, although the rotation of the disc 24 is limited to one way rotation according to the first embodiment, it may be replaced with a normal rotation, a reverse rotation or stoppage of the rotation or an intermittent rotation for setting a predetermined or optional downtime interval, or a normal rotation and the intermittent rotation may be used together.

FIGS. 10(A), 10(B) and 10(C) display the operation display and completion display during the culture program operation, and the magnitude relation among the revolutions of $N_1$ rpm, $N_2$ rpm and $N_3$ rpm of the motor 40 is set at $N_1$ rpm<$N_2$ rpm<$N_3$ rpm and a rising time to reach $N_1$ rpm is set at a, and also a gentle gradient time is set at t when shifting from $N_1$ rpm to $N_2$ rpm, and a gentle gradient time is set at t when shifting from $N_2$ rpm to $N_3$ rpm. That is, an acceleration or deceleration of speed as desired is effected at the gradient time t.

Since such a culture program can be executed, at the time when the cell or tissue is actually cultivated, the matrix 10, in which the cell or tissue is transplanted, is accommodated in the culture chamber 8 while removing the chamber cover 20, then it is placed in the culture housing 80. The chamber cover 20 is closed and the culture unit 4 is fixed to the apparatus body 2. At this time, the motor 40 is moved from the retraction position to the operation position in the direction of X, where it is positioned, then fixed to the apparatus body 2. After a temperature, a humidity, a carbon oxide concentration, an oxygen concentration and so forth in the culture housing 80 are set at proper conditions, the culture fluid 18 having an optimum flow rate for the cell or tissue is supplied to the matrix 10.

When the motor 40 rotates, the magnets 36 are rotated together with the external rotary body 32, and the rotating force of the magnets 36 is transmitted to the disc 24 through the magnetic connection between the magnets 36 and the magnetic bodies 30, that is, the disc 24 is rotated while following the external rotary body 32. The revolution of the disc 24 is given or determined by $N_1$ rpm to $N_3$ rpm of the motor 40. According to the first embodiment, the disc 24 is controlled at the optimum speed, i.e. $N_1$ rpm to $N_3$ rpm as the culture time $T_1$ to $T_3$ elapse, and the disc 24 is rotated at very slow revolution at the beginning of cultivation, and the revolution is increased when the cell gets organized, and then the revolution is further increased at the final stage, thereby controlling the revolution.

Figure 9:
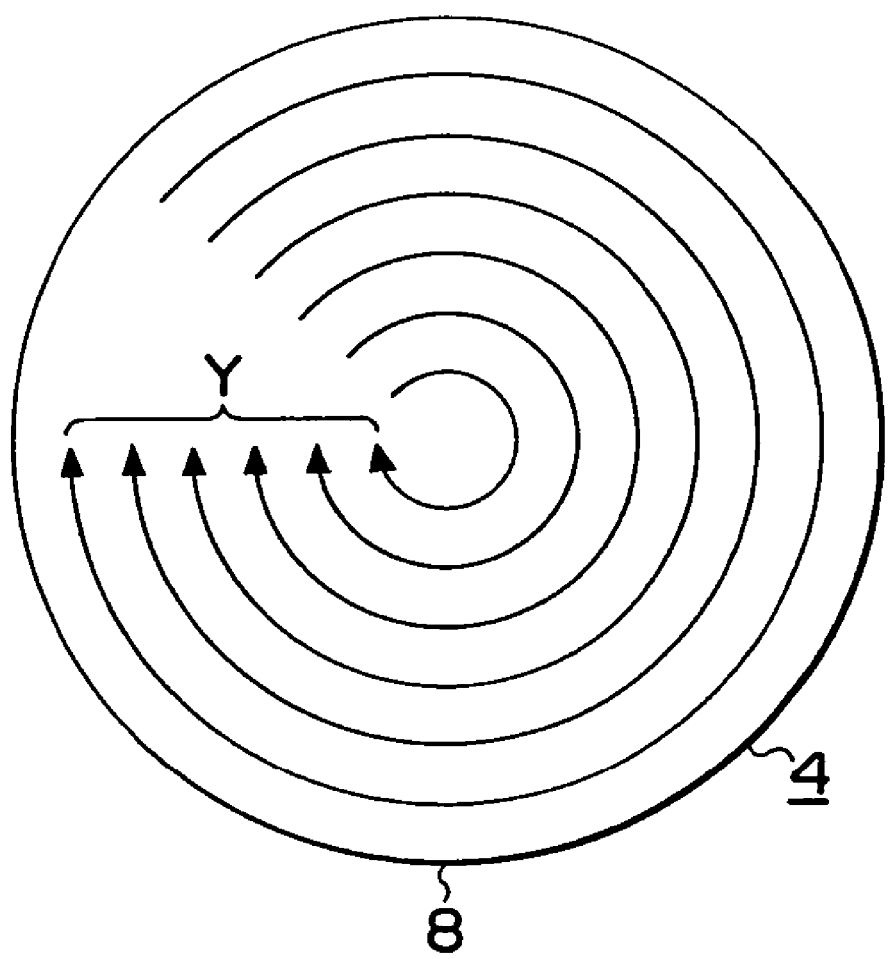
FIG. 9 is a view showing a rotating flow produced in a chamber.

Although a shear stress, which is generated by the rotation of the disc 24 set forth above, is applied to the culture fluid 18 in the culture chamber 8, flow of the culture fluid 18 acts on the surface of the matrix 10, and hence the culture fluid 18 becomes a circumferentially directed flow as shown in FIG. 9 according to the first embodiment. As a result, the cell or tissue on the matrix 10 in the culture chamber 8 proliferates and grows while it is subjected to an application of a shear stress in the circumferential direction of the culture chamber 8.

Figure 11:
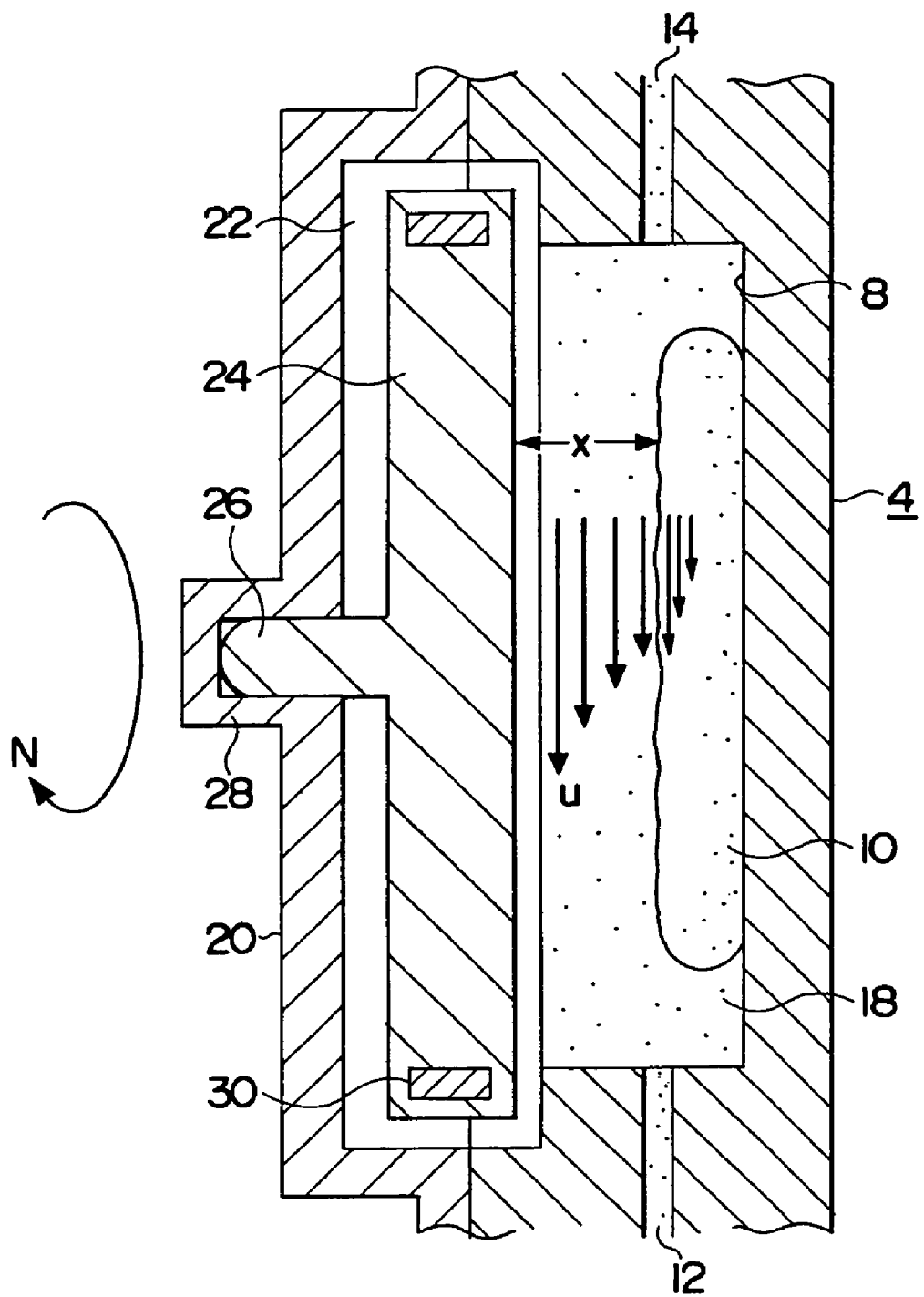
FIG. 11 is a view showing the generation and operation of a shear stress through flow of fluid owing to the rotation of the disc.

Described next with reference to FIG. 11 is a shear stress to be applied to the matrix 10 which is generated by the revolution of the disc 24 at N rpm. When the disc 24 is rotated, fluid flow is generated in the culture fluid 18, and the shear stress $\tau$ generated in the culture fluid 18 is expressed as follows.

$$\tau = \mu \cdot du/dx \qquad (1)$$

where u is a velocity of flow, du is the variation of the velocity of flow, dx is a distance between the surface of the matrix 10 and the disc 24, $\mu$ is viscosity coefficient of the culture fluid 18. Since the matrix 10, which is adhered and fixed to the inner wall of the culture chamber 8 of the culture unit 4, contacts the culture fluid 18 having a viscosity, so that the shear stress $\tau$ is generated on the surface of the matrix 10 or a layer in the vicinity of the surface of the matrix 10 owing to the rotating flow of the culture fluid 18, and hence the shear stress becomes a physical stimulation to contribute to the proliferation and growth of the cell or tissue.

Figure 12:
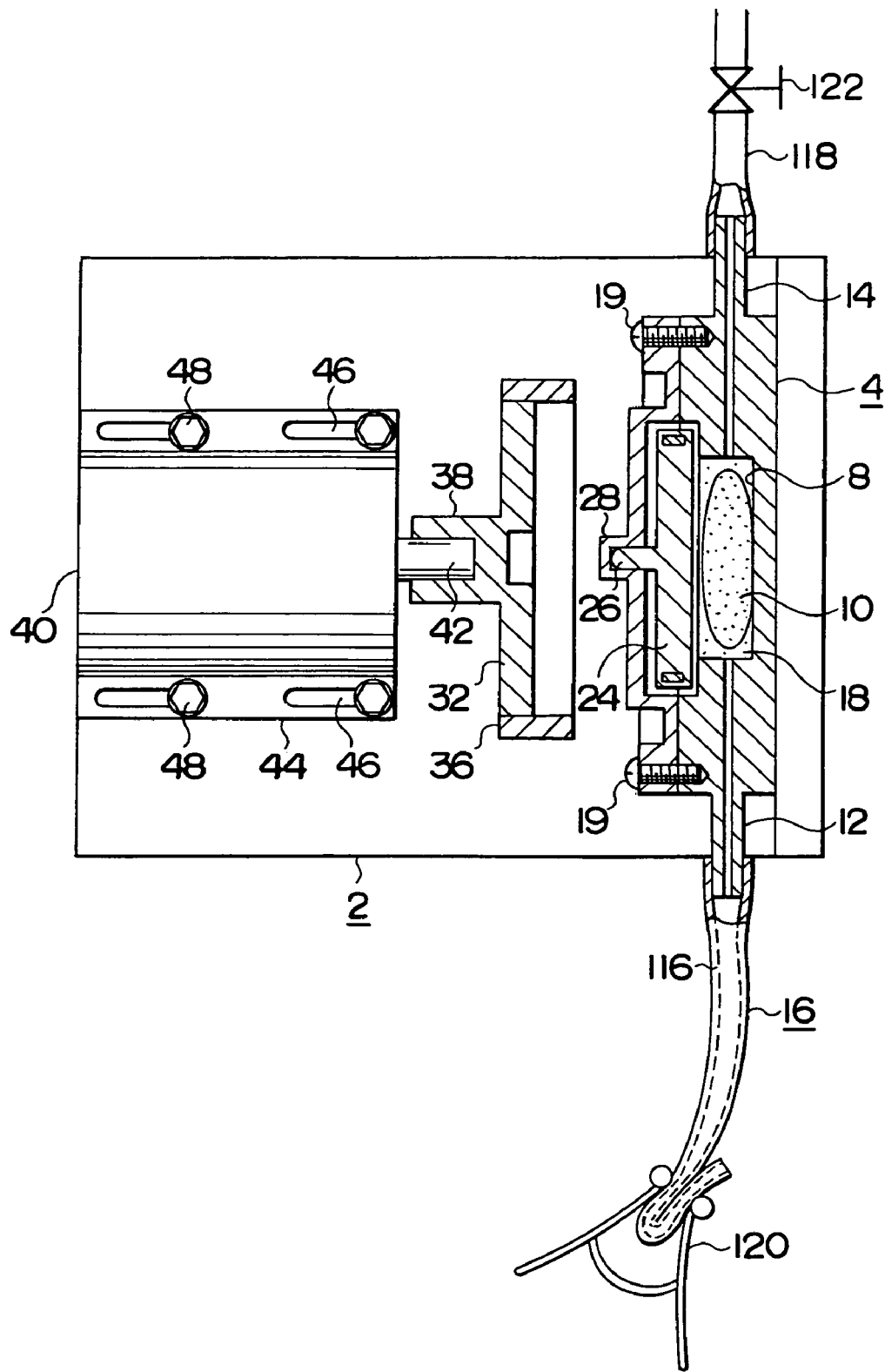
FIG. 12 is a sectional view showing detachable attachment of the culture unit to an apparatus body.

After the execution of the culture program is completed, tubes 116, 118 of the culture circuit 16 connected to the ports 12, 14 of the culture unit 4 are shut as shown in FIG. 12, and a shutting processing is executed by attaching a pinch cock 120 serving as shutting means to the tube 116 side and attaching a cock valve 122 to the tube 118 side.

After the execution of the shutting processing is completed, when the culture unit 4 is detached from the culture circuit 16, the fixing bolts 48 are loosened to remove the motor 40 from the apparatus body 2, then the fixing bolt 56 at the culture unit 4 side is detached from the apparatus body 2 so that the culture unit 4 can be detached or pulled out from the culture circuit 16 and the apparatus body 2.

Since the pinch cock 120 is attached to the tube 116 side to shut the tube 116 while the cock valve 122 at the tube 118 side shuts the tube 118 as set forth above, the culture unit 4 can be separated from the culture circuit 16 and the culture chamber 8 can be held in a hermetically sealed state, thereby preventing the culture fluid 18 from being leaked out from the culture chamber 8. Further, if the culture unit 4 is sterilized by a sterilizing method using an autoclave, and so forth, UV sterilization, gummer rays sterilization, and so forth, the interior of the culture unit 4 can be maintained in an aseptic condition for a long period of time. According to the first embodiment, although the pinch cock 120 and cock valve 122 are employed as means for shutting the tubes 116, 118, they may be substituted by other closing means.

Attachment of the culture unit 4 to the apparatus body 2 and the culture circuit 16 to start next cultivation may be performed by a procedure opposite to the detachment procedure, so that the culture unit 4 can be easily detachably attached to the apparatus body 2 and the culture circuit 16 without contaminating the interior of the culture unit 4, and also the cell or tissue to be cultivated can be surely protected from the contamination of various bacteria and so forth.

Figure 13:
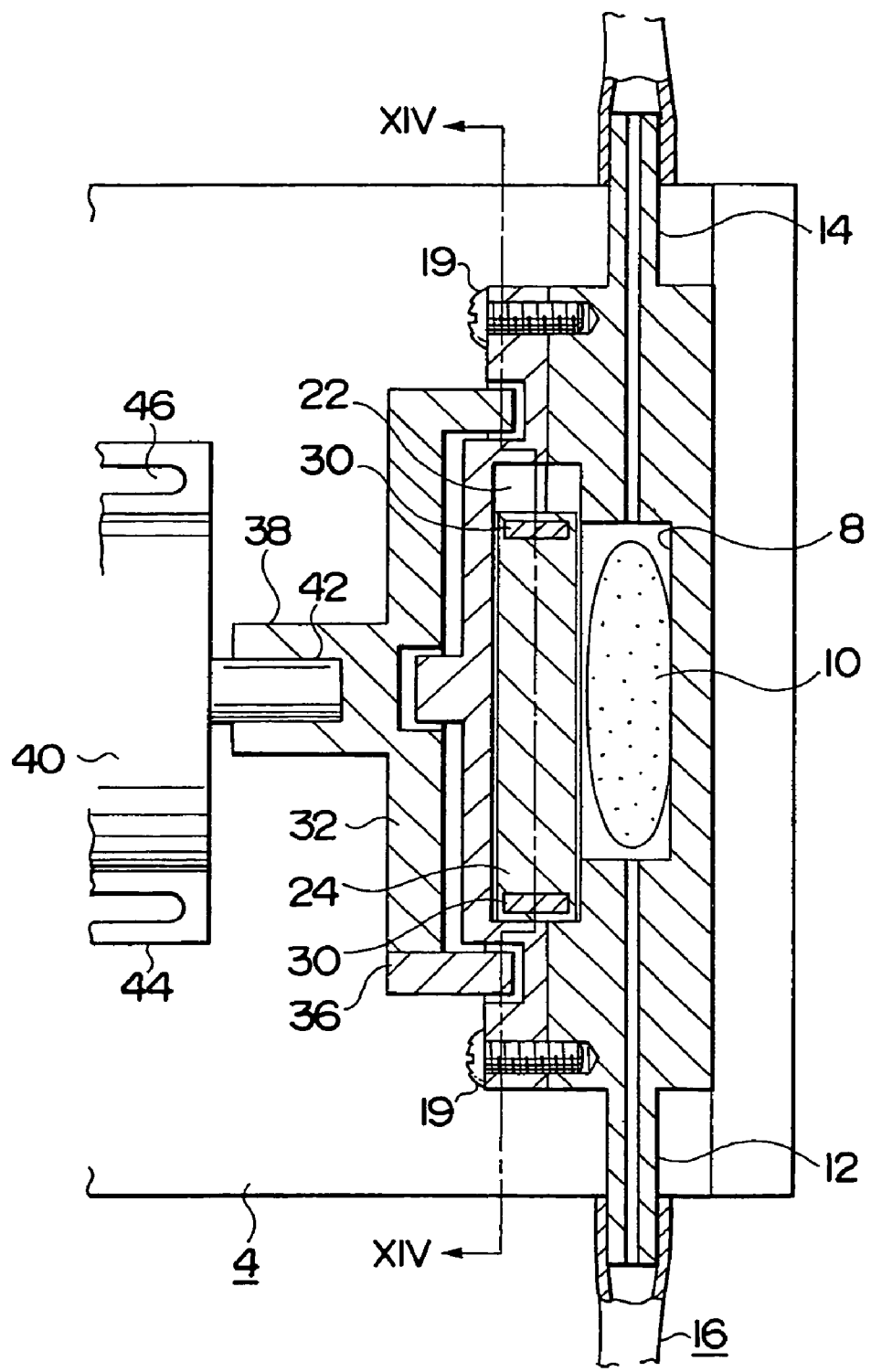
FIG. 13 is a partially sectional view showing a cell/tissue culture apparatus according to a second embodiment of the invention.
Figure 14:
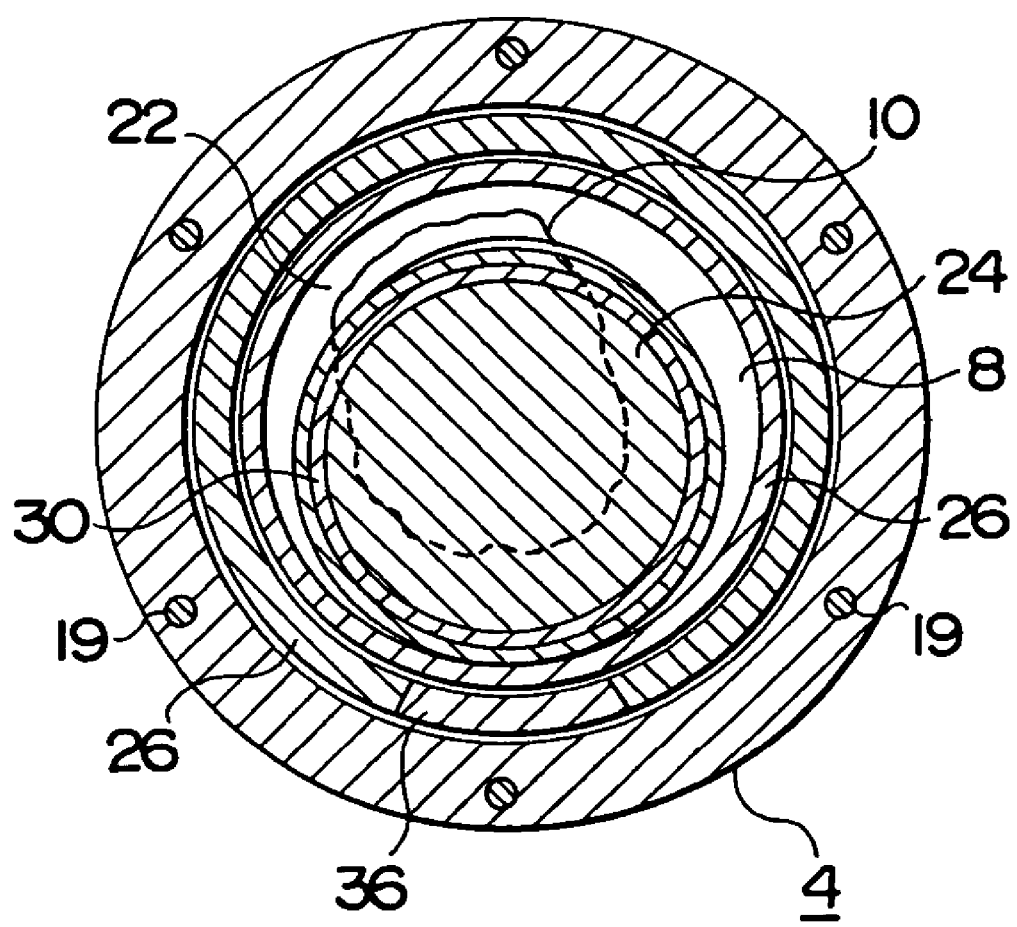
FIG. 14 is a sectional view of a culture unit taken along the ling XIV-XIV shown in FIG. 13.

FIGS. 13 and 14 show a cell/tissue culture apparatus according to a second embodiment of the invention, wherein FIG. 13 shows a main part of a culture unit, and FIG. 14 is a sectional view of the culture unit taken along the line XIV-XIV.

According to the second embodiment, a disc 24 having a diameter which is smaller than an inner diameter of a disc accommodation space 22 is used, and a rotary shaft of the disc 24 can be freely movable in a direction orthogonal to its axis (axial direction) removing the supporting shaft of the disc 24. Annular magnetic bodies 30 are attached to the disc 24 and a single magnet 36 is attached to an external rotary body 32. The configuration of the motor 40 and the attachment construction of the motor 40 are the same as those of the first embodiment.

With such a configuration, when the external rotary body 32 is rotated by the motor 40, the freely rotatable disc 24 is drawn toward the magnets 36 on the external rotary body 32 by the magnetic bodies 30, so that the disc 24 is rotated along the inner wall of the disc accommodation space 22 while it is rotated on its own axis. When the disc 24 is rotated while it is rotated on its axis, flowage having a random flowing direction is generated in the culture fluid 18 in the culture chamber 8, so that the entire surface of the cell or tissue at one side on the matrix 10 receives the shear stress generated by the rotation of the disc 24 through the flowage, and the flowing direction varies every hour.

Figure 15:
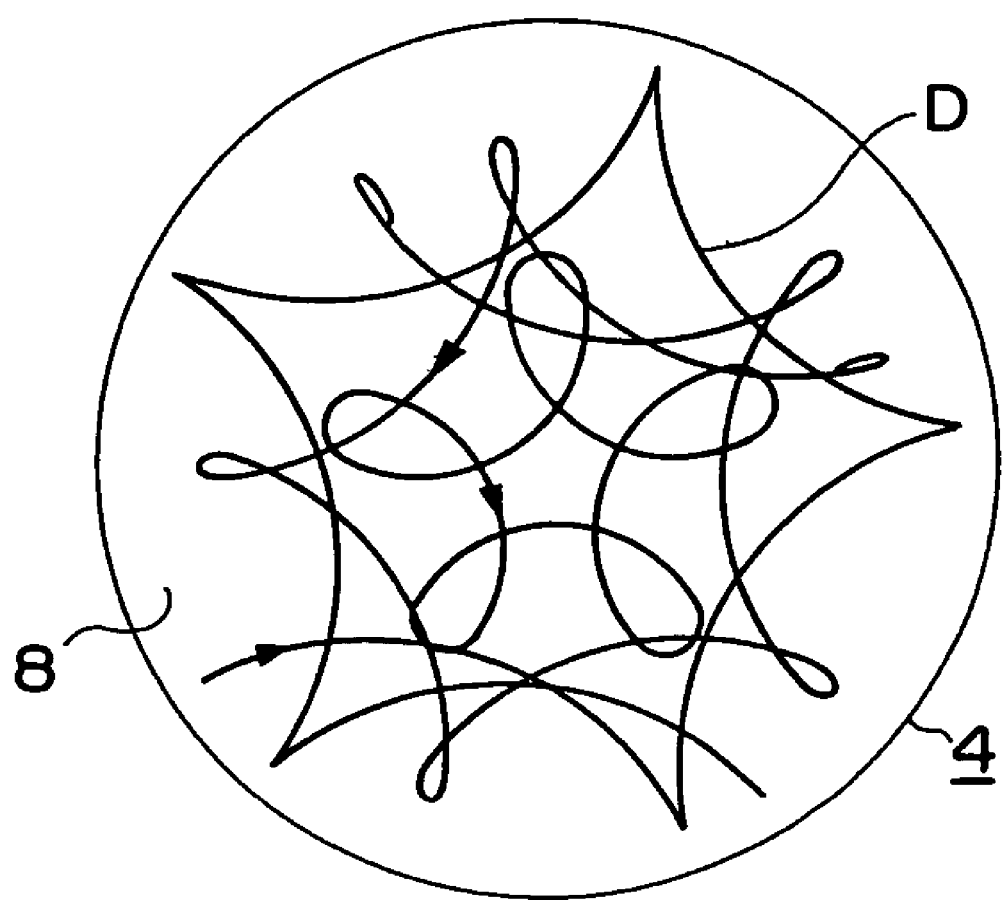
FIG. 15 is a view showing a rotary pattern of a disc in a culture chamber according to the second embodiment of the invention.

Such flowage is illustrated, for example, as shown in FIG. 15, and a track D shows a direction and variation of the shear stress, and such a shear stress is allowed to respond to the culture of the cell or tissue at the part of the living body where the direction of the shear stress is varied.

Figure 10:
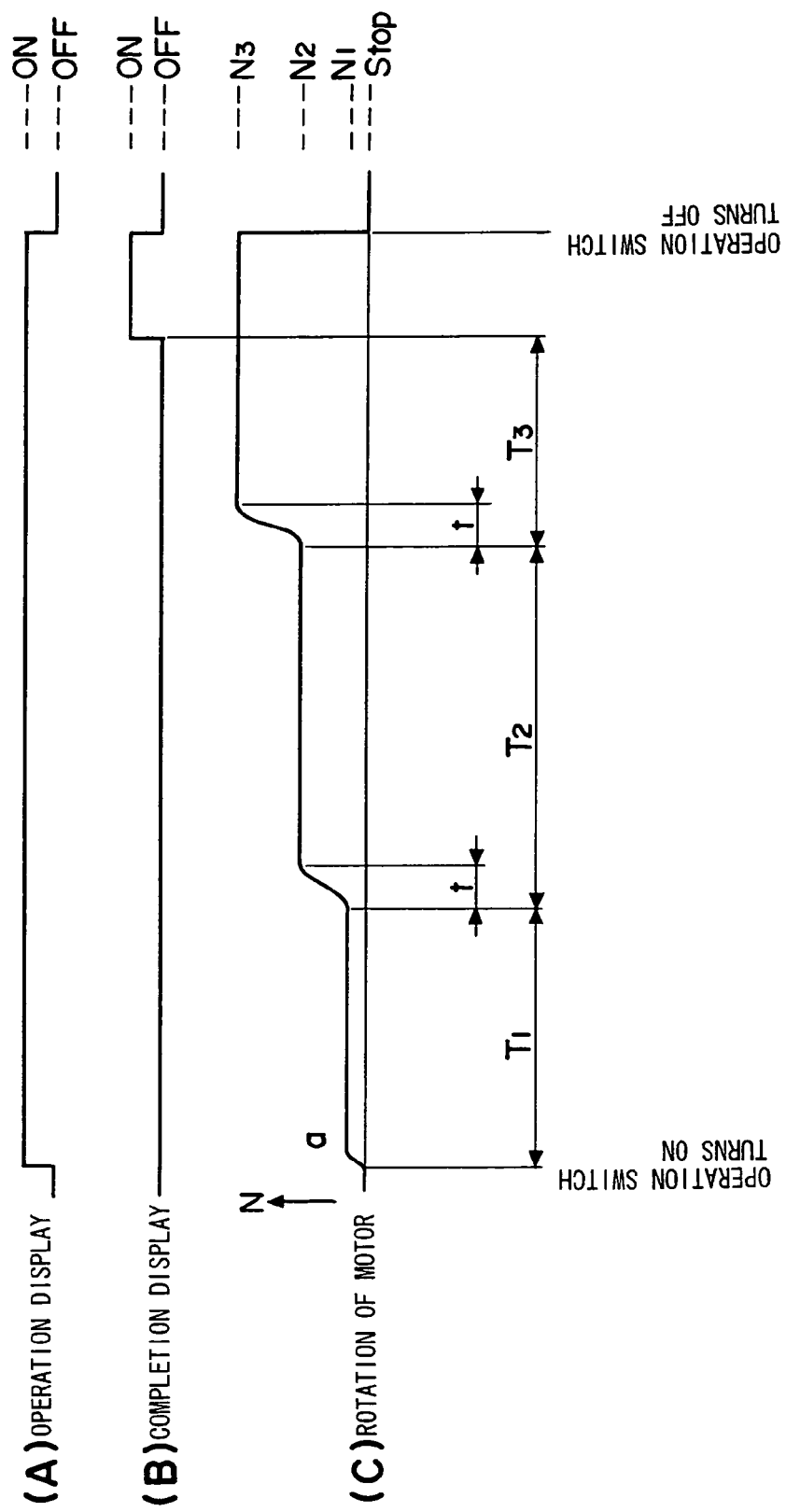
FIG. 10 is a timing chart showing a rotation control operation.

Further, the revolution of the motor 40 is varied as the culture time elapses as represented by the program shown in FIGS. 7 and 8, and the timing chart as shown in FIG. 10, and a rotating speed as desired can be set by the programmed control in the same manner as the first embodiment. Still further, the attachment and detachment of the culture unit 4 relative to the apparatus body is the same as the first embodiment.

Figure 16:
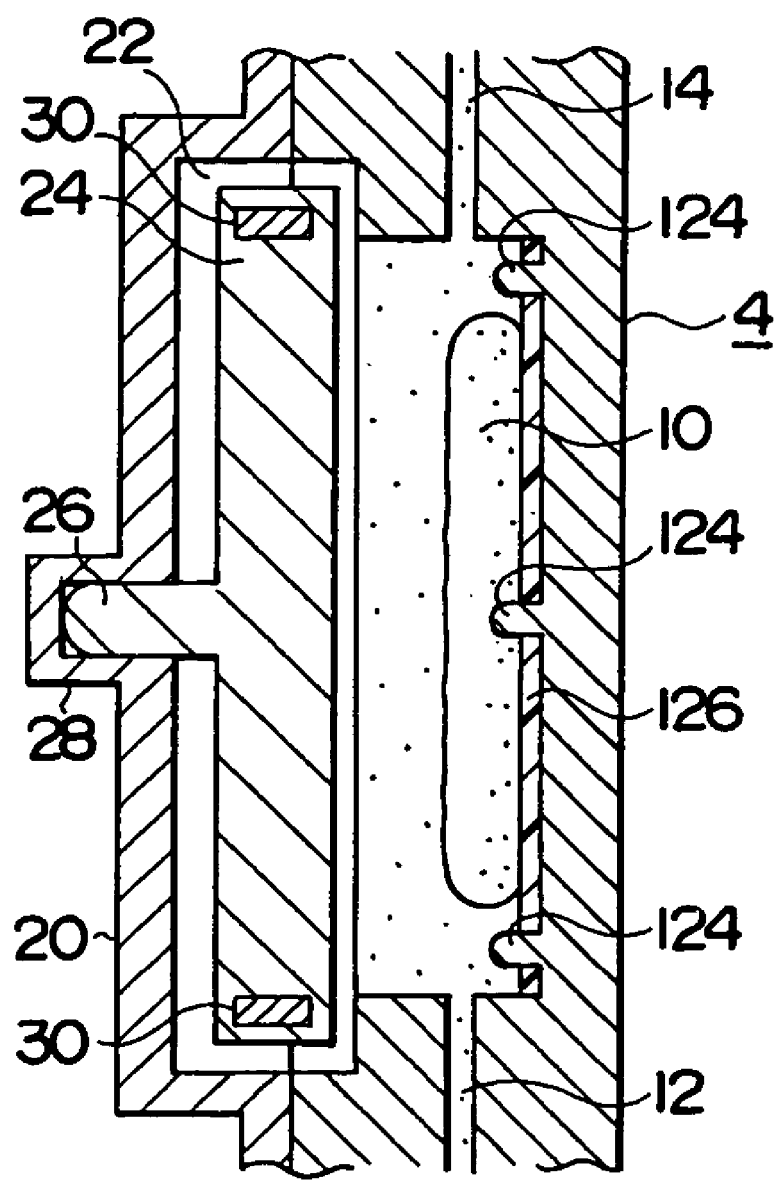
FIG. 16 is a sectional view showing a main part of a culture unit of a cell/tissue culture apparatus according to a third embodiment of the invention.

FIG. 16 shows a cell/tissue culture apparatus according to a third embodiment of the invention.

Although the matrix 10 is directly installed on the inner wall of the culture chamber 8 of the culture unit 4 according to the first and second embodiments, according to the third embodiment, a plurality of fixed projections 124 are projected from an inner wall of a culture chamber 8, and, for example, a plurality of silicone rubber sheets 126 serving as a fixing member relative to a matrix 10 are installed between the fixed projections 124, and the matrix 10 is fixedly positioned and fixed to the surface of the silicone rubber sheets 126.

Still further, according to the first to third embodiments, although the matrix 10 is fixedly positioned on the inner wall of the culture chamber 8 of the culture unit 4, it may be fixedly positioned and fixed to the surface of the disc 24 so that the matrix 10 is rotated together with the disc 24.

Figure 17:
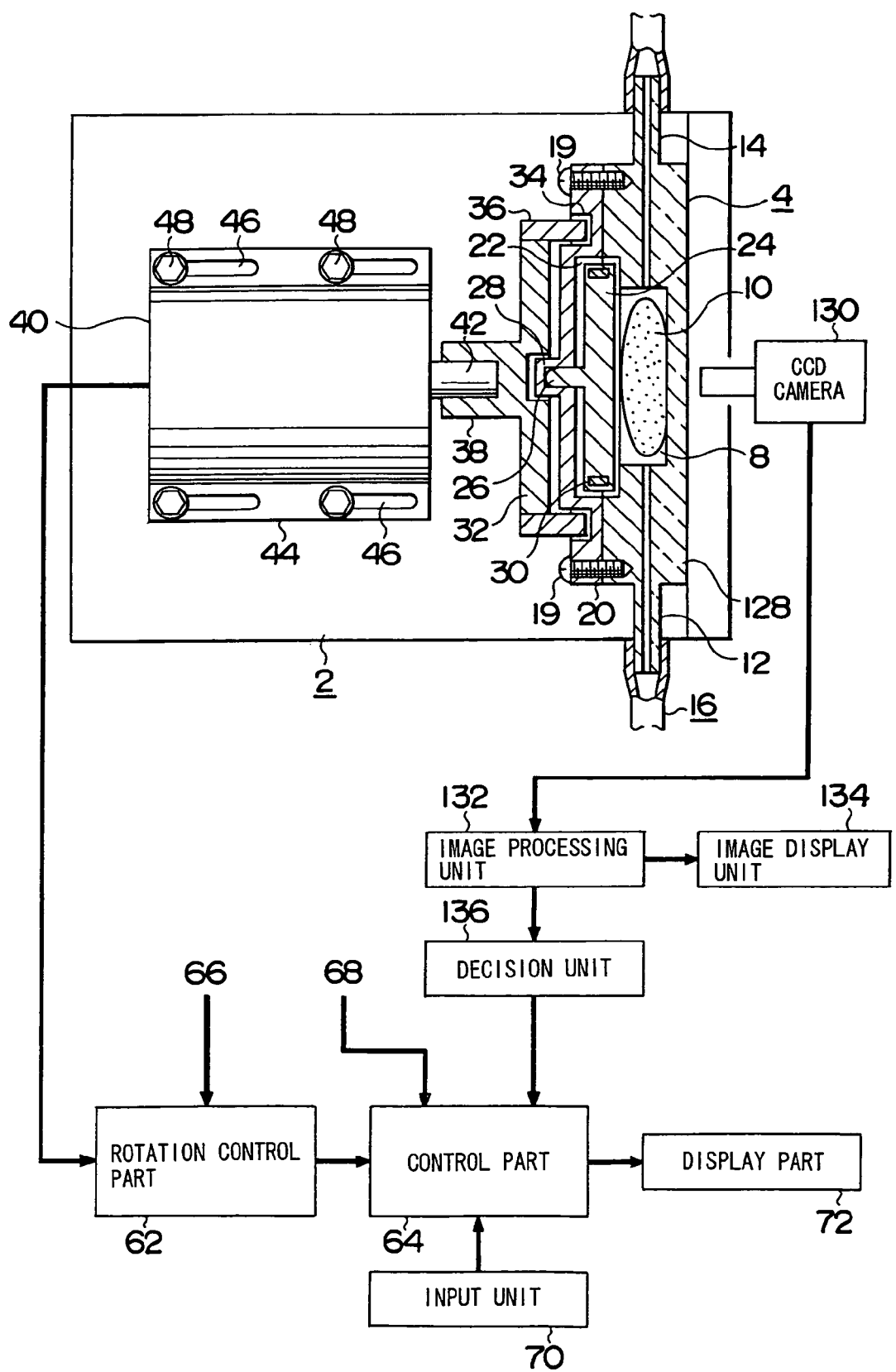
FIG. 17 is a partially sectional view showing a cell/tissue culture apparatus according to a fourth embodiment of the invention.

FIG. 17 shows a cell/tissue culture apparatus according to a fourth embodiment of the invention.

According to the fourth embodiment, a transparent wall 128 is provided on a part or as a whole of a culture unit 4 through which the interior of a culture chamber 8 can be seen, and a CCD camera 130 serving as photographing means for photographing a matrix 10 in the culture chamber 8 is installed in the vicinity of the transparent wall 128, wherein image obtained by the CCD camera 130 is supplied to an image processing unit 132 where the image is processed and the processed image is displayed on an image display unit 134, and it is also supplied to a decision unit 136 as decision information. The decision unit 136 decides the proliferation and growth of the cell or tissue in response to the change of color, the shape and so forth of the matrix 10 based on the processed image, and the result of decision is supplied to a control part 64. Other configurations are the same as those of the controller 60 shown in FIG. 5.

As mentioned above, if the state of the matrix 10 in the culture chamber 8 is grasped as image information, and it is observed through this image information, the proliferation and growth of the cell or tissue on the matrix 10 can be visually grasped, and hence each stage of the growth of the cell or tissue on the matrix 10 can be grasped with accuracy and appropriate processing can be executed corresponding to the state of the proliferation and growth thereof.

As mentioned in detail above, the following effects can be obtained by the invention.

a Since the disc installed in the culture chamber can be rotated in a non-contact state relative to the driving means on its axis with an optional rotary pattern, thereby generating the rotating flow in the culture fluid, a physical stimulation such as a shear stress generated by the rotation of the disc can be applied to the material to be cultivated in the chamber in a non-contact state between the material to be cultivated and the disc. As a result, it is possible to apply the shear stress, which imitates a physical stimulation on the living body, can be applied to the material to be cultivated, thereby contributing to the facilitation of the culture.

b Since the chamber accommodating the material to be cultivated therein can be moved by independently separating from the culture circuit as the culture unit, or by detachably attaching to the culture circuit, thereby protecting the material to be cultivated from the contamination of various bacteria and so forth.

c Since the disc can be rotated with an optional rotary pattern, a physical stimulation as desired can be applied to the material to be cultivated, thereby realizing the application of physical stimulation corresponding to a part on the living body and enhancing the facilitation of the culture.

d Each stage of growth of the cell or tissue can be accurately grasped by the image of the matrix.

Although the configurations, operations and effects of the cell/tissue culture apparatus serving as the mode for carrying out the invention are described with reference to the first to fourth embodiments as illustrated in the attached drawings, the invention is not limited to such a mode for carrying out the invention and the embodiments, but it includes all the configurations, which can be predicted or conjectured by a person skilled in the art, such as various configurations, modifications and so forth which can be conjectured by the object, the mode for carrying out the invention, and the embodiments of the invention.

INDUSTRIAL APPLICABILITY

As mentioned above, the cell/tissue culture apparatus of the invention is useful for the culture technology of the cell or tissue to which a tissue engineering is applied, more particularly it is adapted for performing an in vitro culture of the cell or tissue of a living body such as human body, and is also adapted for efficiently realizing a metabolism function of a cell or tissue and applying a physical stimulation to the material to be cultivated necessary for prolongation, differentiation, and acceleration of a cell.

The invention claimed is:

1. A cell/tissue culture apparatus comprising:
   a culture chamber formed in a culture unit for accommodating therein a material to be cultivated in a stationary state and circulating a culture fluid through ports provided at a side wall of the culture chamber;
   a disc accommodating space formed in the culture unit together with the culture chamber and communicating with the culture chamber, said disc accommodating space being filled with the culture fluid;
   a disc rotatably installed in the culture fluid of the disc accommodating space separately from the material to be cultivated and having a flat face at a face side opposite to the material to be cultivated, wherein a circumferential flow is produced in the culture fluid when the disc is rotated, and a physical stimulation is applied to the material to be cultivated by the circumferential flow; and
   rotary driving means for applying a rotating force to the disc from an outside of the culture chamber in a state where it does not contact the disc, said rotary driving means being provided with an outer periphery part inserted into an annular recess part formed at an outer surface of said culture unit detachably in a non-contact state.

2. A cell/tissue culture apparatus according to claim 1, wherein the physical stimulation is a shear stress.

3. A cell/tissue culture apparatus according to claim 1, wherein the rotary driving means applies the rotating force to the disc, while magnetic coupling means is interposed between the disc and the rotary driving means.

4. A cell/tissue culture apparatus according to claim 1, wherein the rotary driving means is a motor.

5. A cell/tissue culture apparatus according to claim 1, further comprising control means for controlling the rotating force of the rotary driving means with an optional pattern.

6. A cell/tissue culture apparatus according to claim 1, wherein the culture unit in which the culture chamber is formed is rendered in a hermetically sealed state, and the culture unit is attached to and detached from a culture circuit for circulating the culture fluid.

7. A cell/tissue culture apparatus according to claim 1, wherein the disc is set to be smaller in diameter than the disc accommodating space and movable in a direction orthogonal to an axis of said disc.

8. A cell/tissue culture apparatus according to claim 1, further comprising photographing means for photographing the material to be cultivated in the culture chamber.

9. A cell/tissue culture apparatus according to claim 1, further comprising a culture unit which is transparent as a part or as a whole and photographing means, wherein the material to be cultivated is accommodated and cultivated in the chamber formed in the culture unit, and the material to be cultivated can be photographed by the photographing means from an outside of the chamber.

10. A cell/tissue culture apparatus according to claim 1, further comprising:
    fluid supply means for supplying the culture fluid, which absorbed nitrogen, oxygen, carbon dioxide, to an interior of the culture chamber continuously or intermittently; and
    pressure application means for applying a predetermined pressure to the material to be cultivated in the culture chamber continuously, intermittently, or by stages.

* * * * *

UNITED STATES PATENT AND TRADEMARK OFFICE
CERTIFICATE OF CORRECTION

PATENT NO. : 7,399,629 B2 Page 1 of 1
APPLICATION NO. : 10/475183
DATED : July 15, 2008
INVENTOR(S) : Takao Takagi et al.

It is certified that error appears in the above-identified patent and that said Letters Patent is hereby corrected as shown below:

Title Page, Item (75) Inventors:
"Shimizu-ken" should read --Shizuoka-ken--

Signed and Sealed this

Second Day of December, 2008

JON W. DUDAS
*Director of the United States Patent and Trademark Office*